(12) United States Patent
Ono

(10) Patent No.: US 11,122,973 B2
(45) Date of Patent: Sep. 21, 2021

(54) OPHTHALMOLOGICAL APPARATUS

(71) Applicant: TOPCON CORPORATION, Tokyo (JP)

(72) Inventor: Yusuke Ono, Kita-ku (JP)

(73) Assignee: TOPCON CORPORATION, Tokyo (JP)

( * ) Notice: Subject to any disclaimer, the term of this patent is extended or adjusted under 35 U.S.C. 154(b) by 225 days.

(21) Appl. No.: 16/470,989

(22) PCT Filed: Dec. 8, 2017

(86) PCT No.: PCT/JP2017/044184
§ 371 (c)(1),
(2) Date: Jun. 19, 2019

(87) PCT Pub. No.: WO2018/135175
PCT Pub. Date: Jul. 26, 2018

(65) Prior Publication Data
US 2019/0365223 A1 Dec. 5, 2019

(30) Foreign Application Priority Data
Jan. 23, 2017 (JP) .............................. JP2017-009515

(51) Int. Cl.
*A61B 3/12* (2006.01)
*A61B 3/10* (2006.01)
(Continued)

(52) U.S. Cl.
CPC ................ *A61B 3/12* (2013.01); *A61B 3/102* (2013.01); *A61B 3/15* (2013.01); *A61B 3/0008* (2013.01); *A61B 3/103* (2013.01)

(58) Field of Classification Search
CPC .. A61B 3/12; A61B 3/102; A61B 3/15; A61B 3/0008; A61B 3/103; A61B 3/14; A61B 3/10
(Continued)

(56) References Cited

U.S. PATENT DOCUMENTS 5,822,446 A * 10/1998 Kato ...................... G16H 30/20
382/128
2011/0170062 A1 7/2011 Isogai et al.
(Continued)

FOREIGN PATENT DOCUMENTS

EP 2 821 006 A1 1/2015
EP 2821006 A1 * 1/2015 ........... A61B 3/0025
(Continued)

OTHER PUBLICATIONS

Extended European Search Report dated Jul. 20, 2020 in European Application No. 17892116.9.
(Continued)

*Primary Examiner* — Mohammed A Hasan
(74) *Attorney, Agent, or Firm* — Xsensus LLP

(57) ABSTRACT

According to an ophthalmological apparatus of an embodiment example, a light beam projecting system includes an optical scanner and projects a light beam onto an eye fundus. A fixation system projects fixation light onto the eye fundus. A photographing device captures a moving image of the eye fundus onto which the fixation light is being projected, to acquire a front observation image. An analyzing circuitry analyzes the front observation image to specify the position of a predetermined site of the eye fundus. A controlling circuitry controls at least one of the fixation system and the optical scanner based on the positional relationship between the position of the predetermined site specified by the analyzing circuitry and a projection target area of the light beam from the light beam projecting system.

5 Claims, 8 Drawing Sheets

(51) Int. Cl.
    *A61B 3/15*         (2006.01)
    *A61B 3/00*         (2006.01)
    *A61B 3/103*       (2006.01)

(58) Field of Classification Search
    USPC .......................................................... 351/206
    See application file for complete search history.

(56) References Cited

U.S. PATENT DOCUMENTS

| | | |
|---|---|---|
| 2012/0127428 A1 | 5/2012 | Isogai et al. |
| 2015/0010226 A1 | 1/2015 | Kubota et al. |
| 2016/0143523 A1* | 5/2016 | Miyashita ............ A61B 3/0025 351/206 |
| 2016/0360963 A1 | 12/2016 | Kubota et al. |

FOREIGN PATENT DOCUMENTS

| | | |
|---|---|---|
| JP | 2015-128630 A | 7/2015 |
| JP | 2016-158721 A | 9/2016 |

OTHER PUBLICATIONS

International Search Report and Written Opinion dated Feb. 27, 2018 for PCT/JP2017/044184 filed on Dec. 8, 2017, 7 pages including English Translation of the International Search Report.

\* cited by examiner

OPHTHALMOLOGICAL APPARATUS

CROSS-REFERENCE TO RELATED APPLICATIONS

The present application is based on International Patent Application No. PCT/JP2017/044184, filed Dec. 8, 2017, which claims priority to Japanese Patent Application No. 2017-009515, filed Jan. 23, 2017, the entire contents of each of which are incorporated herein by reference.

FIELD

Embodiments described herein relate generally to an ophthalmological apparatus.

BACKGROUND

The ophthalmological apparatuses include ophthalmological imaging apparatuses for eye image acquisition, ophthalmological measurement apparatuses for ocular characteristic measurement and ophthalmological treatment apparatuses for eye treatment.

Examples of the ophthalmological imaging apparatuses include optical coherence tomography (OCT) scanners that acquire cross sectional images using OCT scanning, fundus cameras that capture fundus photographs, scanning laser ophthalmoscopes (SLOs) that acquire fundus images through laser scanning with confocal optical systems, slit lamp microscopes, and surgical microscopes.

Examples of the ophthalmological measurement apparatuses include eye refraction test devices (i.e., refractometers, keratometers) that measure refractive characteristics of eyes, tonometers, specular microscopes that acquire corneal characteristics (e.g., corneal thickness, cell distribution), wave front analyzers that acquire ocular aberration information with Hartmann-Shack sensors, and perimeters/microperimeters that measure visual fields.

Examples of the ophthalmological treatment apparatuses include laser treatment devices that project laser light onto treatment target sites such as diseased sites, surgical devices for specific purposes (e.g., cataract surgery, keratorefractive surgery), and surgical microscopes.

Many ophthalmological apparatuses have the function of presenting a fixation target to a subject's eye (or to its fellow eye). The fixation target has the function of guiding the line of sight to acquire data from a desired site of the eye and the function of fixing the eye during data acquisition.

PATENT DOCUMENT 1: Japanese Unexamined Patent Application Publication No. 2016-158721

SUMMARY

However, there are cases where the data of the desired site may not be acquired even if a fixation target is being presented. For example, the above functions of the fixation target may not be sufficiently exerted when the subject's eye has a visual acuity problem, or when the subject is an elderly person or a child. Also, the voluntary or involuntary movement of the subject's eye may interfere with fixation. Such phenomena are referred to as fixation loss.

A purpose of the present embodiment is to provide an ophthalmological apparatus capable of suitably dealing with fixation loss.

An ophthalmological apparatus of the first aspect of some embodiments includes a light beam projecting system, a fixation system, a photographing device, analyzing circuitry, and controlling circuitry. The light beam projecting system includes an optical scanner and is configured to project a light beam onto a fundus of a subject's eye. The fixation system is configured to project fixation light onto the fundus. The photographing device is configured to capture a moving image of the fundus onto which the fixation light is being projected, to acquire a front observation image. The analyzing circuitry is configured to analyze the front observation image to specify a position of a predetermined site of the fundus. The controlling circuitry is configured to control at least one of the fixation system and the optical scanner based on a positional relationship between the position of the predetermined site specified by the analyzing circuitry and a projection target area of the light beam from the light beam projecting system.

According to an ophthalmological apparatus of the second aspect of some embodiments, the controlling circuitry is configured to control the optical scanner to change the projection target area of the light beam based on the positional relationship between the position of the predetermined site specified by the analyzing circuitry and the projection target area of the light beam from the light beam projecting system.

According to an ophthalmological apparatus of the third aspect of some embodiments, the controlling circuitry is configured to control the fixation system to change a fixation position based on the positional relationship between the position of the predetermined site specified by the analyzing circuitry and the projection target area of the light beam from the light beam projecting system.

According to an ophthalmological apparatus of the fourth aspect of some embodiments, the controlling circuitry is configured to display the front observation image on a display device, and display an image indicating the projection target area of the light beam over the front observation image.

According to an ophthalmological apparatus of the fifth aspect of some embodiments, the controlling circuitry is configured to display an image representing the position of the predetermined site specified by the analyzing circuitry, over the front observation image.

According to an ophthalmological apparatus of the sixth aspect of some embodiments, the controlling circuitry is configured to compare, with a predetermined threshold, a deviation of the position of the predetermined site specified by the analyzing circuitry with respect to the projection target area of the light beam, and execute control for at least one of the fixation system and the optical scanner only when the deviation exceeds the predetermined threshold.

Effect of the Invention

According to the embodiment configured as described above, fixation loss can be treated in a suitable way.

DETAILED DESCRIPTION

Figure 1:
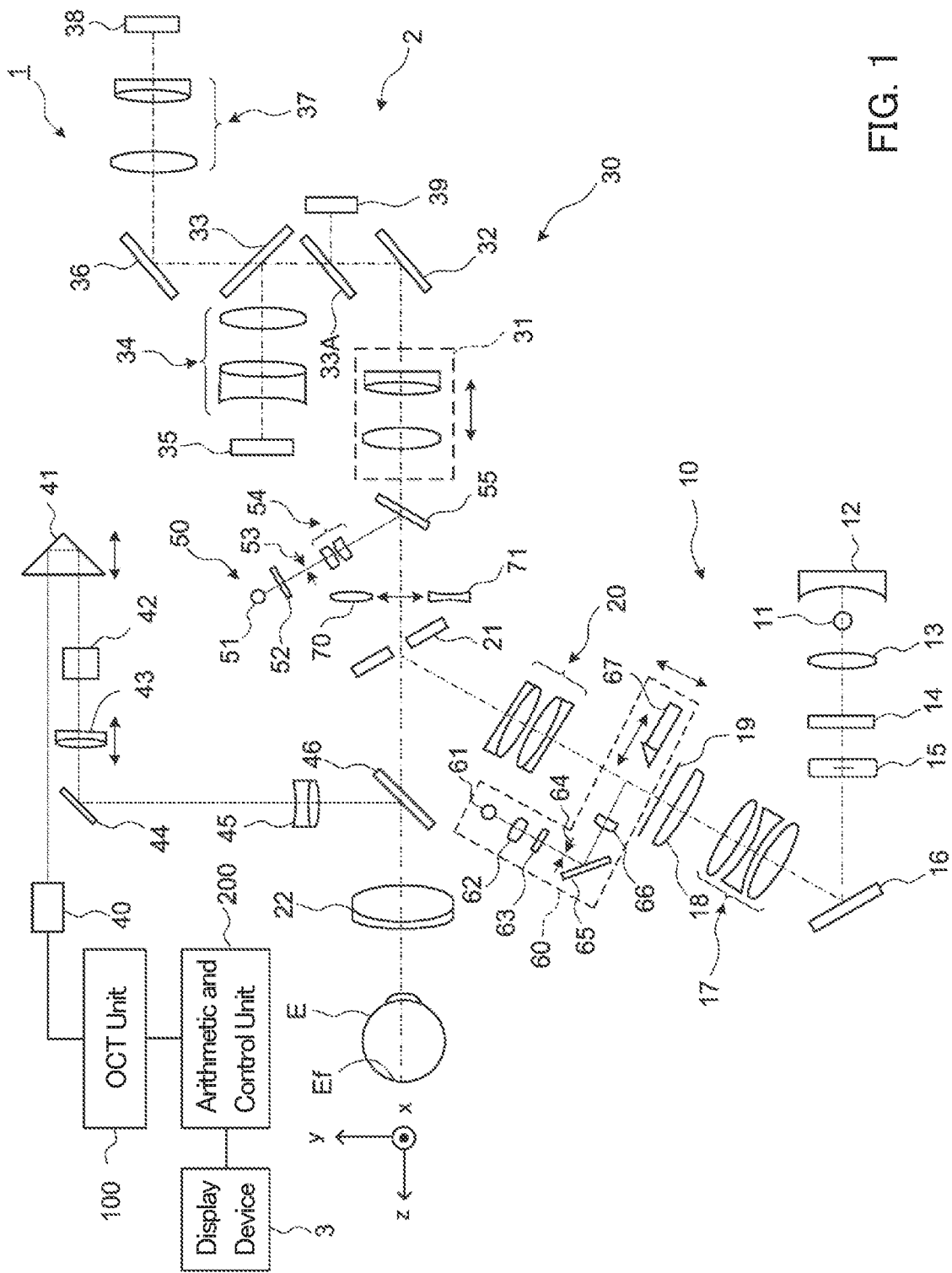
FIG. 1 is a schematic diagram illustrating an example of the configuration of an ophthalmological apparatus according to an embodiment.

Embodiment examples of the present invention will be described in detail with referring to the drawings. The ophthalmological apparatus according to some embodiments at least includes a configuration for obtaining a front observation image of an eye fundus and a configuration for projecting a light beam onto the eye fundus, that is, includes an photographing device and a light beam projecting system.

A front observation image of the fundus is an image representing the morphology of the fundus when the fundus is viewed from the front side (i.e., cornea side), and is a moving image composed of a plurality of image frames. Examples of ophthalmological apparatuses capable of acquiring such a front observation image include fundus cameras, scanning laser ophthalmoscopes, surgical microscopes, slit lamp microscopes, and OCT scanners. When an OCT scanner is employed, for example, a front observation image can be obtained by repeatedly scanning a three dimensional region of the fundus to acquire a plurality of three dimensional images and then rendering these three dimensional images. Hereinafter, the front observation image is sometimes simply referred to as an observation image.

The configuration for projecting the light beam onto the fundus is provided, for example, in any of an ophthalmological imaging apparatus, an ophthalmological measurement apparatus, and an ophthalmological treatment apparatus. The configuration for projecting the light beam onto the fundus includes an optical scanner for deflecting the light beam. Examples of ophthalmological imaging apparatuses including the optical scanner include OCT scanners, and scanning laser ophthalmoscopes. Microperimeters, axial length measurement apparatuses, and retinal characteristic measurement apparatuses are examples of ophthalmological measurement apparatuses including the optical scanner. Laser treatment devices (photocoagulators) are an example of ophthalmological treatment apparatuses with the optical scanner.

Ophthalmological apparatuses according to some embodiments may include other configurations in addition to the configuration for acquiring front observation images of the fundus and the configuration for projecting light beams onto the fundus.

The ophthalmological apparatus according to the embodiment example described below includes a fundus camera and an OCT scanner. Swept source OCT is adopted to the OCT scanner in the embodiment example, however the type of OCT is not limited to this, and other OCT types (e.g., spectral domain OCT, time domain OCT, en-face OCT) may be adopted to other embodiment examples.

<Configuration>

As shown in FIG. 1, the ophthalmological apparatus 1 includes the fundus camera unit 2, the OCT unit 100 and the arithmetic and control unit 200. The fundus camera unit 2 is provided with optical systems and mechanisms for acquiring front images of the subject's eye E. The OCT unit 100 includes part of optical systems and part of mechanisms for performing OCT scanning. Another part of the optical systems and another part of the mechanisms for performing OCT scanning are provided in the fundus camera unit 2. The arithmetic and control unit 200 includes one or more processors that execute various calculations and controls. In addition to these, the ophthalmological apparatus 1 may also include any elements and/or units such as a member for supporting the subject's face (e.g., a chin rest, a forehead rest) and a lens unit for switching the sites subjected to OCT scanning. The lens unit is, for example, an attachment for anterior eye segment OCT scanning.

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a memory circuit or a memory device.

<Fundus Camera Unit 2>

The fundus camera unit 2 is provided with an optical system for photographing the fundus Ef of the subject's eye E. Images of fundus Ef (referred to as fundus images, fundus photographs, or the like) obtained include front images such as observation images and photographed images. An observation image is obtained by capturing a moving image using near-infrared light. A photographed image is a still image obtained by using flash light. Further, the fundus camera unit 2 is capable of capturing front images (anterior eye segment images) by photographing the anterior eye segment of the subject's eye E.

The fundus camera unit 2 includes the illumination optical system 10 and the photographing optical system 30. The illumination optical system 10 projects illumination light onto the subject's eye E. The photographing optical system 30 detects the return light of the illumination light from the subject's eye E. The measurement light incident from the OCT unit 100 is directed to the subject's eye E through the optical path in the fundus camera unit 2, and the return light thereof is directed to the OCT unit 100 through the same optical path.

The light output from the observation light source 11 of the illumination optical system 10 (referred to as observation illumination light) is reflected by the reflection mirror 12 having a curved reflective surface, passes through the condenser lens 13, and becomes near-infrared light after passing through the visible cut filter 14. Further, the observation illumination light is once converged near the photographing light source 15, reflected by the mirror 16, and passes through the relay lenses 17 and 18, the diaphragm 19, and the relay lens 20. Then, the observation illumination light is reflected on the peripheral part (i.e., the surrounding area of the aperture part) of the aperture mirror 21, penetrates the dichroic mirror 46, and is refracted by the objective lens 22, thereby illuminating the subject's eye E (the fundus Ef or the anterior eye segment thereof). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the return light passes through the half mirror 33A, is reflected by the dichroic mirror 33, and forms an image on the light receiving surface of the image sensor 35 by the condenser lens 34. The image sensor 35 detects the return light at a predetermined frame rate. Note that the focus of the photographing optical system 30 is regulated to coincide with the fundus Ef or the anterior eye segment.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to the dichroic mirror 33, passes through the dichroic mirror 33, is reflected by the mirror 36, and forms an image on the light receiving surface of the image sensor 38 by the condenser lens 37.

The liquid crystal display (LCD) 39 displays a fixation target and a visual acuity measurement target. Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

The fixation position of the subject's eye E can be changed by changing the display position of the fixation target on the screen of the LCD 39. Examples of the fixation position include the followings: a fixation position for acquiring an image centered on the macula; a fixation position for acquiring an image centered on the optic nerve head; a fixation position for acquiring an image centered on the fundus center that is located between the macula and the optic nerve head; and a fixation position for acquiring an image of a site far away from the macula (periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, capable of changing the fixation position, to the subject's eye E is not limited to display devices such as an LCD. For example, the fixation target that is capable of changing the fixation position can be generated by lighting one (or more) of the plurality of light sources in a light source array (e.g., a light emitting diode (LED) array) in a selective manner. Optionally, the fixation target that is capable of changing the fixation position can be generated by employing one or more movable light sources.

The alignment optical system 50 generates an alignment indicator used for the alignment of the optical system with respect to the subject's eye E. The alignment light output from the LED 51 travels through the diaphragm 52, the diaphragm 53, and the relay lens 54, is reflected by the dichroic mirror 55, and passes through the aperture part of the aperture mirror 21. The light having passed through the aperture part of the aperture mirror 21 penetrates the dichroic mirror 46, and is projected onto the subject's eye E via the objective lens 22. The cornea reflection light of the alignment light passes through the same route as that of the return light of the observation illumination light and is guided to the image sensor 35. Based on the received image (referred to as the alignment indicator image), manual alignment and/or automatic alignment can be performed.

The focus optical system 60 generates a split indicator used for the focus adjustment with respect to subject's eye E. In conjunction with the movement of the photography focusing lens 31 along the optical path of the photographing optical system 30 (referred to as the photographing optical path), the focus optical system 60 is moved along the optical path of the illumination optical system 10 (referred to as the illumination optical path). The reflection rod 67 can be inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64, is reflected by the mirror 65, and is converged on the reflective surface of the reflection rod 67 by the condenser lens 66. Further, the focus light travels through the relay lens 20, is reflected by the aperture mirror 21, and penetrates the dichroic mirror 46, thereby being projected onto the subject's eye E via the objective lens 22. The fundus reflection light of the focus light passes through the same route as the cornea reflection light of the alignment light and is guided to the image sensor 35. Based on the image (referred to as the split indicator image), manual focusing and/or automatic focusing can be performed.

The diopter correction lenses 70 and 71 can be selectively inserted into the position in the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT scanning together. The dichroic mirror 46 reflects the light of wavelength bands used for OCT scanning and transmits the light for fundus photography. Listed from the OCT unit 100 side to the dichroic mirror 46 side, the collimator lens unit 40, the optical path length changing device (OPL changing device) 41, the optical scanner 42, the OCT focusing lens 43, the mirror 44, and the relay lens 45 are arranged in the OCT optical path (the optical path of the measurement light).

The OPL changing device 41 is movable in the directions indicated by the arrow in FIG. 1, whereby the length of the OCT optical path is changed. The change in the optical path length can be utilized for correcting the optical path length according to the axial length, and for regulating the interference condition, for example. The OPL changing device 41 includes a corner cube and a mechanism for moving the corner cube.

The optical scanner 42 is placed at a position optically conjugate with the pupil of the subject's eye E. The optical scanner 42 deflects the measurement light LS passing through the OCT optical path. The optical scanner 42 is, for example, a Galvano mirror scanner capable of two dimensional scanning.

The OCT focusing lens 43 is moved along the optical path of the measurement light LS in order to perform the focus adjustment of the optical system for OCT. The movement of the photography focusing lens 31, the movement of the focus optical system 60, and the movement of the OCT focusing lens 43 can be controlled in an interlocking manner.

<OCT Unit 100>

Figure 2:
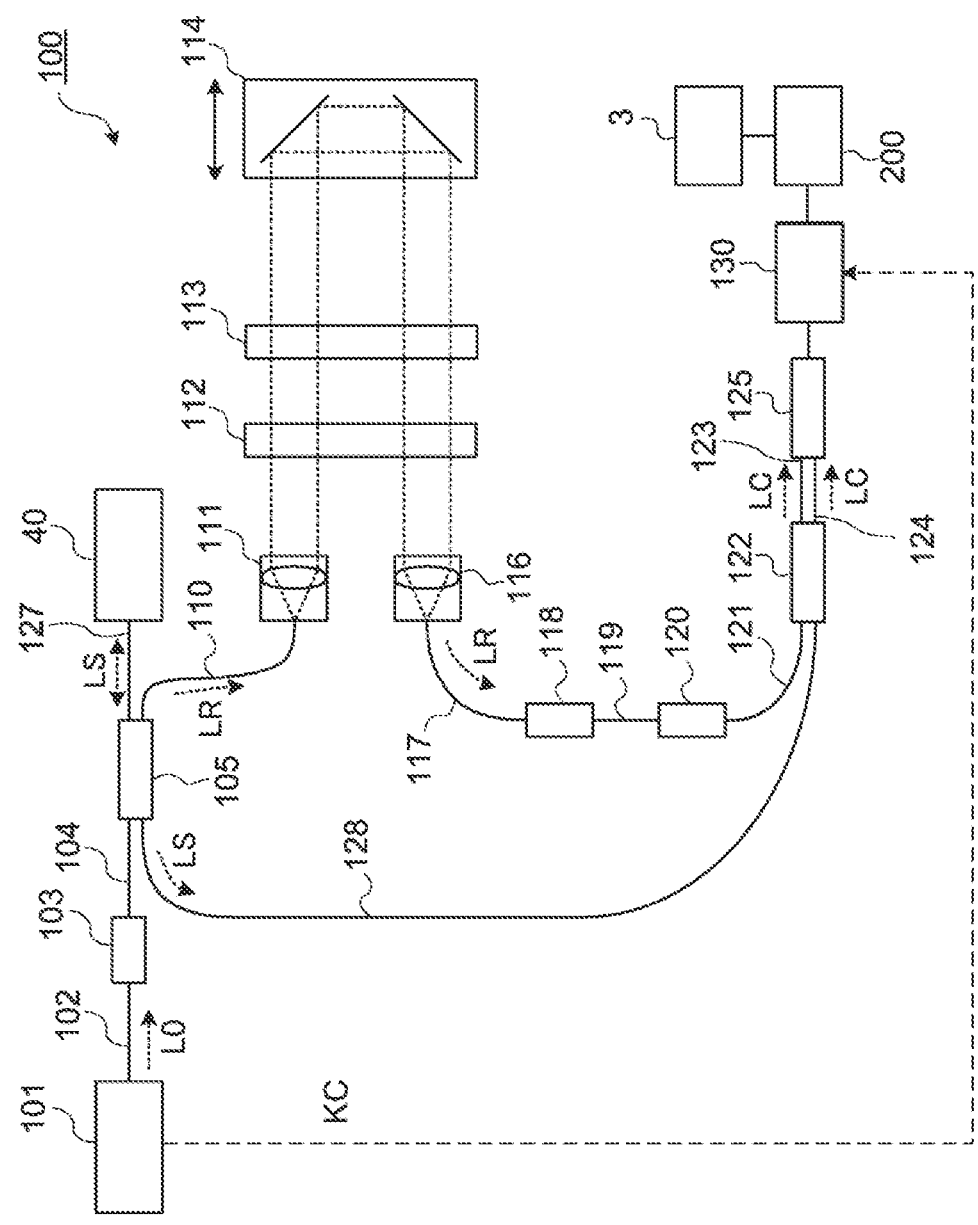
FIG. 2 is a schematic diagram illustrating an example of the configuration of the ophthalmological apparatus according to the embodiment.

As illustrated in FIG. 2, the OCT unit 100 is provided with the optical system for performing swept source OCT. The optical system includes an interference optical system. The interference optical system has the function of splitting the light emitted from the light source of wavelength tunable type (also referred to as wavelength swept type) into measurement light and reference light, the function of superposing the return light of the measurement light from the subject's eye E and the reference light having traveled through the reference optical path to generate interference light, and the function of detecting the interference light. The result of the detection (i.e., detection signal) of the interference light obtained by the interference optical system is a signal representing a spectrum of the interference light. The detection signal is sent to the arithmetic and control unit 200.

The light source unit 101 includes, for example, a near infrared tunable laser configured to change the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR.

The reference light LR is guided through the optical fiber 110 to the collimator 111, is converted into a parallel light beam, travels through the optical path length correction member 112 and the dispersion compensation member 113, and is guided to the corner cube 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other. The corner cube 114 is movable in the incident direction of the reference light LR, whereby the optical path length of the reference light LR is changed.

The reference light LR that has passed through the corner cube 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the OPL changing device 41, the optical scanner 42, the OCT focusing lens 43, the mirror 44, and the relay lens 45, and then reaches the dichroic mirror 46. The measurement light LS is reflected by the dichroic mirror 46, is refracted by the objective lens 22, and is incident on the subject's eye E. The measurement light LS is reflected and scattered at various depth positions of the subject's eye E. The return light of the measurement light LS from the subject's eye E travels along the same route as the outward way in the opposite direction, is directed to the fiber coupler 105, and then reaches the fiber coupler 122 via the optical fiber 128.

The fiber coupler 122 couples (superposes) the measurement light LS incident through the optical fiber 128 and the reference light LR incident through the optical fiber 121, to generate interference light. The fiber coupler 122 splits the interference light at a predetermined splitting ratio (e.g., 1:1) to generate a pair of interference light LC. The pair of the interference light LC is guided to the detector 125 through the optical fibers 123 and 124, respectively.

The detector 125 is, for example, a balanced photodiode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the DAQ 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, optically delays one of the two pieces of split light, generates the combined light of the two pieces of split light, and generates the clock KC based on the result of the detection of the combined light. The DAQ 130 performs the sampling of the detection signal input from the detector 125 based on the clock KC. The DAQ 130 sends the result of the sampling of the detection signal from the detector 125 to the arithmetic and control unit 200.

The present example is provided with both the OPL changing device 41 for changing the length of the optical path of the measurement light LS (referred to as the measurement optical path or the measurement arm) and the corner cube 114 for changing the length of the optical path of the reference light LR (referred to as the reference optical path or the reference arm). However, only one of the OPL changing device 41 and the corner cube 114 may be provided. Another optical element may be employed to change the difference between the measurement optical path length and the reference optical path length.

<Control System>

Figure 3A:
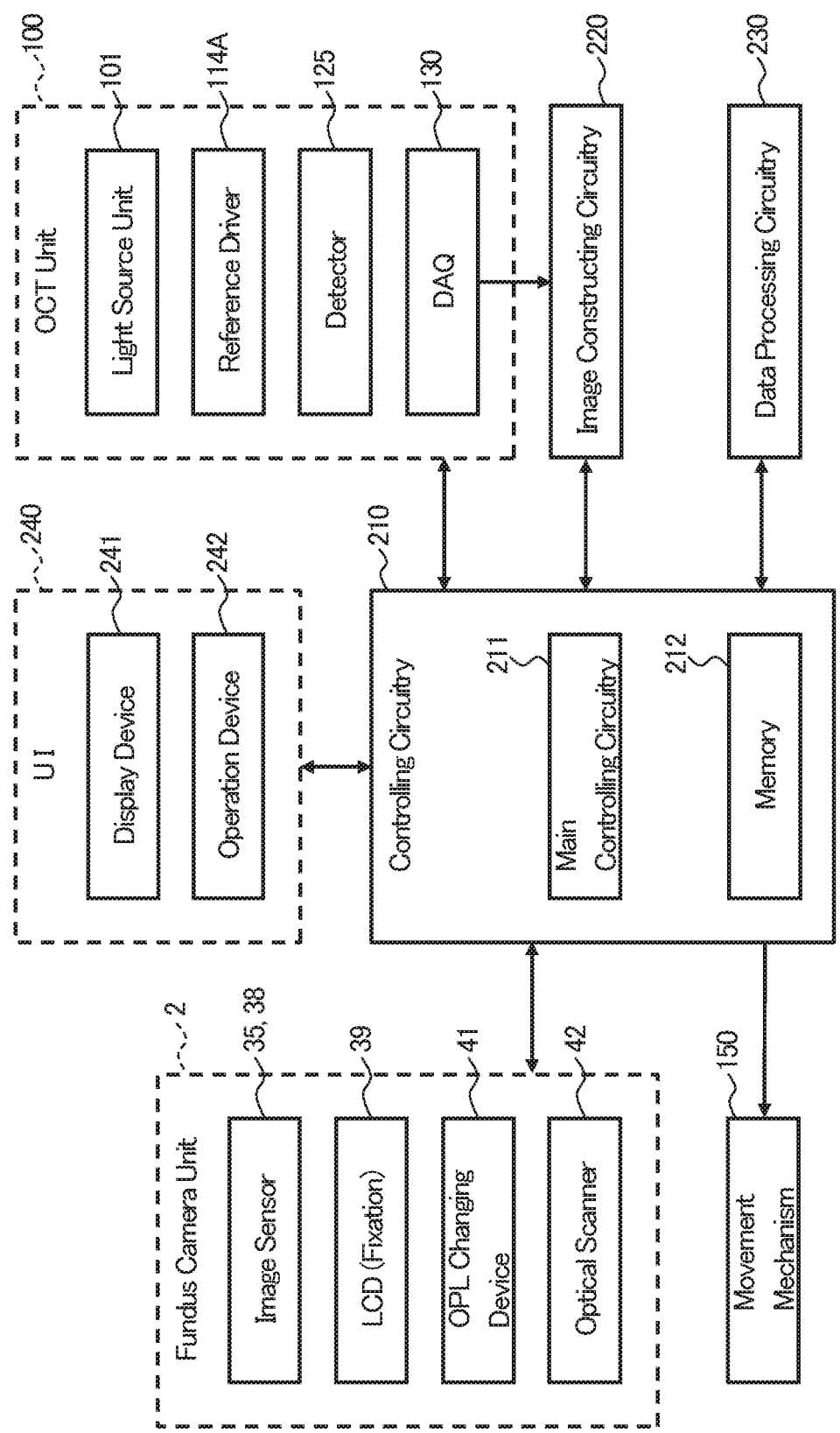
FIG. 3A is a schematic diagram illustrating an example of the configuration of the ophthalmological apparatus according to the embodiment.
Figure 3B:
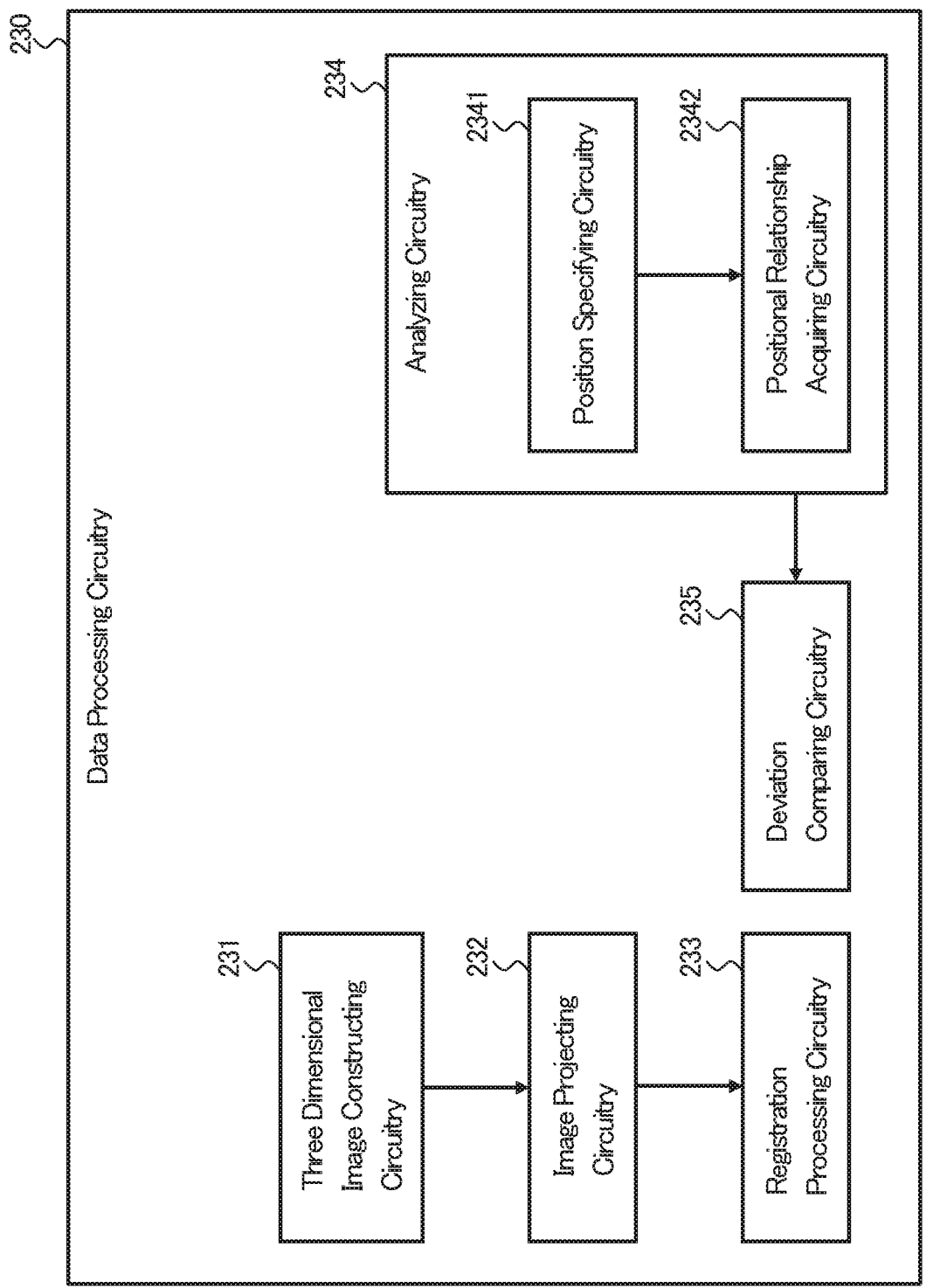
FIG. 3B is a schematic diagram illustrating an example of the configuration of the ophthalmological apparatus according to the embodiment.

FIG. 3A and FIG. 3B show examples of the configuration of the control system of the ophthalmological apparatus 1. FIG. 3A and FIG. 3B omit some of the components included in the ophthalmological apparatus 1. The controlling circuitry 210, the image constructing circuitry 220 and the data processing circuitry 230 are provided, for example, in the arithmetic and control unit 200.

<Controlling Circuitry 210>

The controlling circuitry 210 performs various kinds of controls. The controlling circuitry 210 includes the main controlling circuitry 211 and the memory 212.

<Main Controlling Circuitry 211>

The main controlling circuitry 211 includes a processor(s), and controls each part of the ophthalmological apparatus 1 (including each component shown in FIG. 1 to FIG. 3B). For example, the main controlling circuitry 211 moves the photography focusing lens 31 by controlling a driving mechanism (not shown in figures). Further, the main controlling circuitry 211 moves the OCT focusing lens 43 by controlling a driving mechanism (not shown in figures). In addition, the main controlling circuitry 211 moves the corner cube 114 by controlling the reference driver 114A.

The movement mechanism 150 moves, for example, at least the fundus camera unit 2 in a three dimensional manner. In a typical example, the movement mechanism 150 includes the followings: a mechanism for moving at least the fundus camera unit 2 in the x direction (i.e., left and right direction); a mechanism for moving at least the fundus camera unit 2 in the y direction (i.e., up and down direction); and a mechanism for moving at least the fundus camera unit 2 in the z direction (i.e., depth direction, front and back direction). The mechanism for moving at least the fundus camera unit 2 in the x direction includes, for example, an x stage movable in the x direction and an x movement mechanism that moves the x stage. The mechanism for moving at least the fundus camera unit 2 in they direction includes, for example, a y stage movable in the y direction and a y movement mechanism that moves the y stage. The mechanism for moving at least the fundus camera unit 2 in the z direction includes, for example, a z stage movable in the z direction and a z movement mechanism that moves the z stage. Each of the movement mechanisms includes an actuator such as a pulse motor and operates under the control of the main controlling circuitry 211.

The main controlling circuitry 211 controls the LCD 39. For example, the main controlling circuitry 211 displays a fixation target at a position on the screen of the LCD 39 corresponding to the manually or automatically set fixation position. Further, the main controlling circuitry 211 can change (in a continuous or stepwise manner) the display position of the fixation target displayed on the LCD 39, whereby the fixation target can be moved (i.e., the fixation position can be changed). The display position and movement mode of the fixation target are set manually or automatically. The manual setting is performed using a GUI, for example. The automatic setting is performed by the data processing circuitry 230, for example.

<Memory 212>

The memory 212 stores various kinds of data. Examples of the data stored in the memory 212 includes OCT images, fundus images, anterior eye segment images, and subject's eye information. The subject's eye information includes subject information such as the patient ID and the patient's name, identification information for the left eye and the right eye, and electronic medical record information.

<Image Constructing Circuitry 220>

The image constructing circuitry 220 includes a processor, and constructs an image based on the output from the DAQ 130 (that is, based on the result of the detection signal sampling). For example, as in the conventional swept source OCT, the image constructing circuitry 220 applies signal processing to the spectral distribution formed from the sampling result for each A-line to form the reflection intensity profile for each A-line. Then, the image constructing circuitry 220 creates a plurality of pieces of image data from the reflection intensity profiles for a plurality of A-lines and arranges the plurality of pieces of image data along a scan line(s). The aforementioned signal processing includes noise elimination (or noise reduction), filtering, and fast Fourier transform (FFT), for example.

<Data Processing Circuitry 230>

The data processing circuitry 230 includes a processor, and applies image processing and/or analysis to the image constructed by the image constructing circuitry 220. The data processing circuitry 230 includes the three dimensional image constructing circuitry 231, the image projecting circuitry 232, the registration processing circuitry 233, the analyzing circuitry 234, and the deviation comparing circuitry 235.

<Three Dimensional Image Constructing Circuitry 231>

The three dimensional image constructing circuitry 231 operates when OCT scanning has been performed on a three dimensional region of the subject's eye E (in other words, when OCT scanning has been performed for acquiring a three dimensional image).

Note that when OCT scanning of a three dimensional region has not been performed, the three dimensional image constructing circuitry 231, the image projecting circuitry 232 and the registration processing circuitry 233 do not operate.

Examples of scan modes (i.e., scan patterns) for three dimensional region scanning include raster scan (three dimensional scan), radial scan, and multi-cross scan. The raster scan is a mode of scanning a plurality of lines parallel to each other in a sequential manner. The radial scan is a mode of scanning a plurality of radially arranged lines in a sequential manner. The multi-cross scan is a mode of scanning a first line group consisting of a predetermined number of lines parallel to each other and a second line group consisting of a predetermined number of lines orthogonal to the first line group in a sequential manner.

The types of three dimensional image constructed by the three dimensional image constructing circuitry 231 is arbitrary. A three dimensional image typically means an image in which the pixel position are defined using a three dimensional coordinate system. In an embodiment example, three dimensional image constructing circuitry 231 constructs stack data or volume data as three dimensional images.

Stack data is constructed by embedding a plurality of cross sectional images (B-scan images, for example, xz cross sectional images) constructed by the image constructing circuitry 220 based on data acquired by three dimensional region scanning, into a single three dimensional coordinate system (that is, into a single three dimensional space). In other words, stack data is obtained by arranging a plurality of B-scan images obtained along a plurality of scan lines in a three dimensional manner, based on the positional relationship of the scan lines.

Volume data is constructed by interpolation and voxelization of pixels between a plurality of B-scan images included in stack data. Volume data is also referred to as voxel data.

When displaying the three dimensional image constructed in this way, the data processing circuitry 230 can perform rendering. Examples of the rendering include volume rendering and maximum intensity projection (MIP).

The data processing circuitry 230 can construct a two dimensional cross sectional image from the three dimensional image. Multi-planar reconstruction (MPR) is an example of this process.

<Image Projecting Circuitry 232>

The image projecting circuitry 232 constructs front projection images from the three dimensional images constructed by the three dimensional image constructing circuitry 231. A front projection image is a two dimensional image constructed by projecting a three dimensional image in a predetermined direction. The three dimensional image projection processing includes a process of adding the values of a plurality of pixels arranged along the predetermined direction.

Projection images and shadowgrams are typical examples of front projection images. A projection image is constructed by projecting a three dimensional image in a predetermined direction (i.e., the z direction, depth direction, A-scan direction). As with fundus images obtained by the fundus camera unit 2, the surface morphology (surface appearance) of the fundus Ef is represented in a front projection image constructed from a three dimensional image of the fundus Ef.

A shadowgram is constructed by projecting part of a three dimensional image (e.g., partial data corresponding to a specific layer) in a predetermined direction. Projecting partial data including the surface tissue of the fundus Ef (e.g., the inner limiting membrane and layers in the vicinity thereof) yields a front projection image in which the surface morphology of the fundus Ef is represented like fundus images.

<Registration Processing Circuitry 233>

The registration processing circuitry 233 performs registration between the fundus image obtained by the fundus camera unit 2 and the front projection image constructed by the image projecting circuitry 232.

When an observation image is obtained by the fundus camera unit 2, the registration processing circuitry 233 can perform registration for each of the image frames sequentially acquired as the observation image. Alternatively, registration may be performed at a predetermined frame interval.

When a series of OCT scans (e.g., raster scan) is performed in an iterative manner, the image constructing circuitry 220 and the three dimensional image constructing circuitry 231 construct three dimensional images from a series of data acquired in each of the series of OCT scans performed in a sequential manner. More specifically, the image constructing circuitry 220 and the three dimensional image constructing circuitry 231 iteratively perform processing for constructing three dimensional images in synchronization with the iteration of the series of OCT scans. Further, the image projecting circuitry 232 can construct a front projection image from each of the sequentially constructed three dimensional images. The registration processing circuitry 233 can apply registration to each of the front projection images sequentially constructed.

In the case where an observation image is obtained by the fundus camera unit 2 and a series of OCT scans is iteratively performed, the registration processing circuitry 233 can pair an image frame of the observation image and a front projection image based on the frame rate of the observation image and the iteration rate (repetition rate) of the series of OCT scans, and then apply registration to each of the pairs. At this time, the main controlling circuitry 211 can synchronize the acquisition timings of the image frames of the observation image and the iteration timings of the series of OCT scans with each other.

The registration includes, for example, the followings: the first process of detecting feature regions from the both images (i.e., the fundus image and the front projection image); and the second process of applying registration to the both images with the both feature regions as references.

The feature regions detected in the first process may be, for example, any of the followings: a region corresponding to the optic nerve head; a region corresponding to the macula; a region corresponding to a feature blood vessel; a region corresponding to a lesioned part; and a region corresponding to a laser treatment scar. In the first process, the registration processing circuitry 233 can detect feature regions with reference to the pixel values and the pixel arrangements.

In the second process, the registration processing circuitry 233 adjusts the relative position between the fundus image and the front projection image to match the feature region detected from the fundus image and the feature region detected from the front projection image with one another, for example. At this time, the registration processing circuitry 233 may specify the contours or representative points (e.g., the center point, the center of gravity) of the feature region and perform registration to coincide the both contours or the both representative points with one another. In addition, the registration processing circuitry 233 may evaluate the degree of coincidence of the both feature regions, and determine that the both feature regions coincide with one another if the calculated evaluation value is equal to or greater than a predetermined threshold.

<Analyzing Circuitry 234>

The analyzing circuitry 234 analyzes the observation image of the fundus Ef acquired by the fundus camera unit 2 (i.e., the illumination optical system 10 and the photographing optical system 30) to specify the position of a predetermined site of the fundus Ef. The shift of a scan area and/or the movement of the fixation target is performed based on the positional relationship between the position of the predetermined site specified by the analyzing circuitry 234 and a target area for OCT scanning.

Here, the predetermined site of the fundus Ef may be any site. For example, the predetermined site may be the macula, the optic nerve head, a lesioned part, an interested blood vessel, or the like.

Further, the position of the predetermined site specified by the analyzing circuitry 234 may be, for example, a position in the observation image acquired by the fundus camera unit 2 (i.e., a position in its image frame).

The analyzing circuitry 234 includes the position specifying circuitry 2341 and the positional relationship acquiring circuitry 2342.

<Position Specifying Circuitry 2341>

The position specifying circuitry 2341 specifies the position of the predetermined site of the fundus Ef by analyzing the observation image acquired by the fundus camera unit 2. This process is sequentially performed, for example, on at least part of a plurality of image frames included in the observation image.

The position specifying circuitry 2341 specifies the position of the predetermined site of the fundus Ef based on the pixel values (e.g., brightness values) included in the image frames. This position specifying process includes, for example, any known image processing such as thresholding on brightness values, binarization, edge detection, pattern matching, noise removal, morphological operation, and labeling.

In a typical example, in order to specify an image of the optic nerve head, the position specifying circuitry 2341 can use thresholding to search for pixels each having a brightness value that exceeds a predetermined threshold. Alternatively, in order to specify an image of the optic nerve head, the position specifying circuitry 2341 can use binarization, edge detection, pattern matching, etc. to search for an image region of substantially elliptical shape.

Further, the position specifying circuitry 2341 can specify the position of the predetermined site of the fundus Ef, for example, based on any information on the specified image of the predetermined site such as its position, size, shape, etc. Sites specifiable (detectable) with such processing are the optic nerve head (its center, its center of gravity, its outer edge, a rectangle circumscribing the outer edge, etc.) and lesioned parts (their centers, centers of gravity, outer edges, rectangles circumscribing the outer edges, etc.), etc.

When images of two (or more) sites of the fundus Ef have been specified, for example, the position specifying circuitry 2341 may specify the position of the predetermined site of the fundus Ef based on any information on these images such as their positions, relative positions, sizes, relative sizes, shapes, relative shapes, etc. Sites specifiable (detectable) with such processing are the optic nerve head (its center, its center of gravity, its outer edge, a rectangle circumscribing the outer edge, etc.) and a lesioned part (its centers, its center of gravity, its outer edge, a rectangle circumscribing the outer edges, etc.), etc.

<Positional Relationship Acquiring Circuitry 2342>

The positional relationship acquiring circuitry 2342 determines the positional relationship between the position of the predetermined site of the fundus Ef specified by the position specifying circuitry 2341 and the scan target area for OCT scanning.

Here, the scan target area may be set in an arbitrary manner. For example, the scan target area may be an alignment target area for OCT scanning, part or all of the area on which OCT scanning is performed, or part or all of the area of an image frame of an observation image.

In a typical example, the positional relationship acquiring circuitry 2342 can determine the deviation of the position of the predetermined site of the fundus Ef with respect to the scan target area. Here, the deviation of the position of the predetermined site of the fundus Ef with respect to the scan target area is substantially equal to the deviation of the scan target area with respect to the position of the predetermined site of the fundus Ef.

For example, the positional relationship acquiring circuitry 2342 can determine the difference (e.g., the deviation vector) between the position of the predetermined site of the fundus Ef and a preset position in the scan target area. More specifically, the positional relationship acquiring circuitry 2342 determines any one of the followings: the deviation vector whose initial point is placed at the position of the predetermined site of the fundus Ef and whose terminal point is placed at the preset position in the scan target area; and the deviation vector whose initial point is placed at the preset position in the scan target area and whose terminal point is placed at the position of the predetermined site of the fundus Ef.

The preset position in the scan target area may be set in an arbitrary manner. For example, the preset position in the scan target area is set to any of the center of the scan target area, the position in which a plurality of scan lines intersect, and a position on the outer edge of the scan target area (e.g., apex position, middle point position of a side, etc.).

The preset position in the scan target area may be a region having a certain size. For example, a certain region containing the center of the scan target area may be set as the preset position. Alternatively, the outer edge of the scan target area may be set as the preset position.

In such cases, the positional relationship acquiring circuitry 2342 may be configured to determine, for example, a deviation vector that is oriented along the shortest distance line between the position of the predetermined site of the fundus Ef and the certain region in the scan target area. In another example, the positional relationship acquiring circuitry 2342 may be configured to determine a deviation vector that connects the position of the predetermined site of the fundus Ef and a representative position (e.g., the center, the center of gravity, a position on the outer edge, etc.) in the certain region.

Similarly, the position of the predetermined site of the fundus Ef may be a region having a certain size. For example, the positional relationship acquiring circuitry 2342 may be configured to determine a deviation vector based on a region whose center is the position specified by the position specifying circuitry 2341 (e.g., a circular region, a rectangular region, etc.) and a preset position in the scan target area. The size of that region is determined by, for example, the imaging magnification, the size of the scan target area, etc.

Both the preset position in the scan target area and the position of the predetermined site of the fundus Ef may be regions of certain sizes. In such cases, the positional relationship acquiring circuitry 2342 can determine the positional relationship between the both regions.

For example, the positional relationship acquiring circuitry 2342 can determine whether or not the region of the predetermined site of the fundus Ef (e.g., the papillary center of gravity and the vicinity thereof) is located inside the outer edge of the scan target area. This determination is, for example, substantially the same processing as the determination regarding the magnitude of the difference between the position of the predetermined site of the fundus Ef (e.g., the papillary center of gravity) and the center of the scan target area.

<Deviation Comparing Circuitry 235>

The deviation comparing circuitry 235 compares the deviation determined by the positional relationship acquiring circuitry 2342 with a predetermined threshold. This deviation is, for example, the magnitude of the deviation vector described above. The deviation comparing circuitry 235 determines, for example, whether or not the deviation determined by the positional relationship acquiring circuitry 2342 exceeds the predetermined threshold.

The predetermined threshold may be set in an arbitrary manner. For example, the predetermined threshold can be set to a small value in order to improve the precision of the fixation.

<User Interface 240>

The user interface 240 includes the display device 241 and the operation device 242. The display device 241 includes the display device 3. The operation device 242 includes various kinds of operation devices and input devices.

The user interface 240 may include, for example, a device, like a touch panel, having the display function and the operation function. In another embodiment, the ophthalmological apparatus may not include at least part of the user interface. For example, the display device may be an external device connected to the ophthalmological apparatus.

<Operation>

Figure 4:
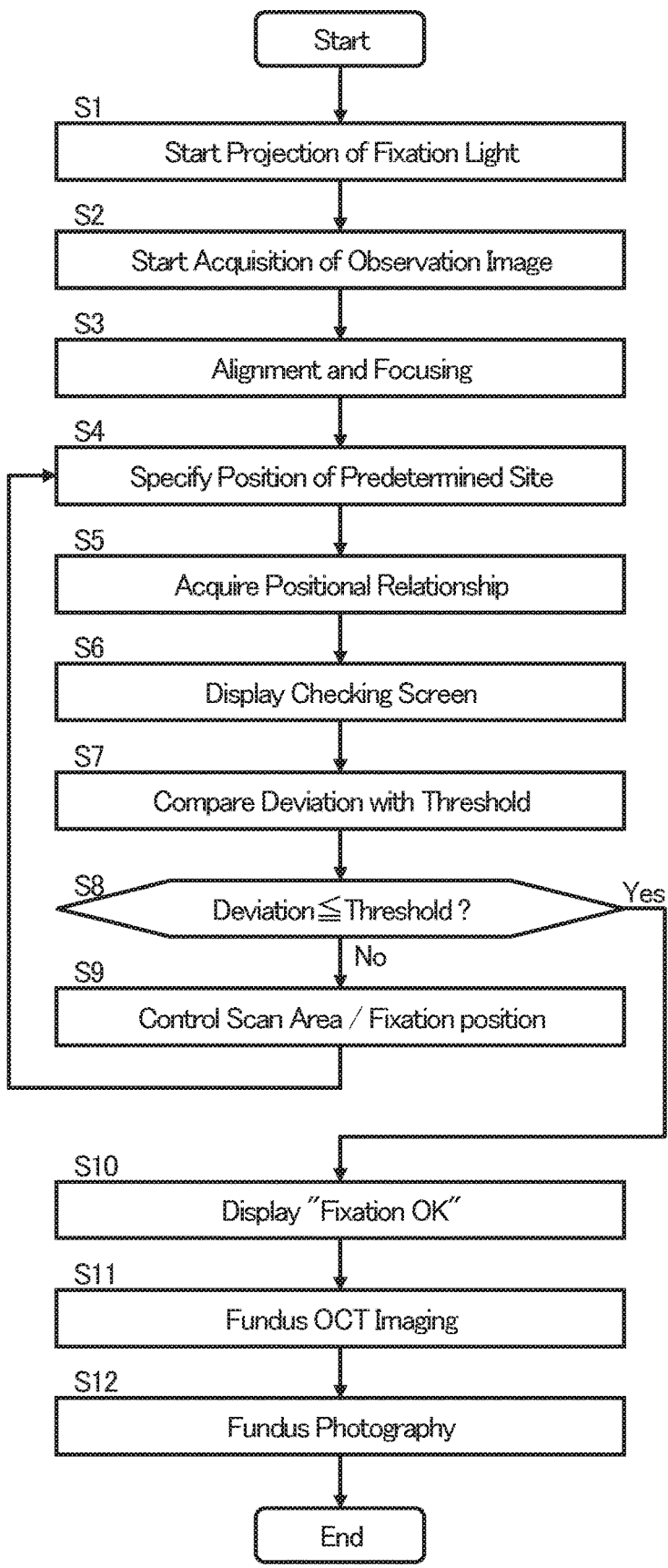
FIG. 4 is a flowchart showing an example of the operation of the ophthalmological apparatus according to the embodiment.

The operation of the ophthalmological apparatus 1 will be described. An example of the operation is shown in FIG. 4.

(S1: Start Projection of Fixation Light)

First, the fixation position is designated. The fixation position designation is performed manually or automatically. In a typical example of manual designation, the main controlling circuitry 211 displays a GUI for fixation position designation on the display device 241. The user uses the GUI and the operation device 242 to set a desired fixation position. In a typical example of automatic designation, the main controlling circuitry 211 designates a fixation position based on information input from the outside. Examples of the information include the electronic medical record of the subject input from the electronic medical record system, and the imaging mode designated manually or automatically. In the present example, it is assumed that "optic nerve head" is designated as the fixation position.

The main controlling circuitry 211 controls the LCD 39 to display the fixation target at the position on the screen corresponding to the designated fixation position. Thereby, fixation light is projected onto the subject's eye E. The fixation light is, for example, continuously projected onto the subject's eye E until the completion of imaging.

(S2: Start Acquisition of Observation Image)

The main controlling circuitry 211 controls the illumination optical system 10 and the photographing optical system 30 to start acquisition of an observation image of the subject's eye E. As described above, the observation image is a moving image obtained by photographing the subject's eye E from the front side. At this stage, an observation image of the anterior eye segment is obtained.

The main controlling circuitry 211 displays the observation image on the display device 241 in real time. Further, the main controlling circuitry 211 transfers image frames sequentially obtained as the observation image to the data processing circuitry 230.

In addition, the timing of starting fixation light projection (step S1) and the timing of starting observation image acquisition (step S2) are not limited to the order shown in FIG. 4. For example, the main controlling circuitry executes control to start fixation target projection after the commencement of observation image acquisition. Alternatively, the main controlling circuitry executes control to simultaneously start observation image acquisition and fixation target projection.

(S3: Alignment and Focusing)

Next, the main controlling circuitry 211 controls the alignment optical system 50 to project alignment light onto the subject's eye E, and controls the focus optical system 60 to project focus light onto the subject's eye E.

Further, the main controlling circuitry 211 performs automatic alignment and automatic focusing in the same manner as in a conventional case. Alternatively, the user may perform one or both of manual alignment and manual focusing. Thereby, the alignment and focusing with respect to the fundus Ef are completed.

At a middle stage in step S3, the observation image obtained by the fundus camera unit 2 shifts from an anterior eye segment observation image to a fundus observation image.

(S4: Specify Position of Predetermined Site)

After completing the alignment and focusing, the position specifying circuitry 2341 specifies the position of the predetermined site of the fundus Ef by analyzing the observation image whose acquisition has started in step S2. In the present example, the position specifying circuitry 2341 specifies the position of the optic nerve head. The position specified is assumed to be the papillary center of gravity position. The result of position specification performed by the position specifying circuitry 2341 is sent to the positional relationship acquiring circuitry 2342.

(S5: Acquire Positional Relationship)

The positional relationship acquiring circuitry 2342 determines the positional relationship (deviation vector) between the position of the predetermined site of the fundus Ef specified by the position specifying circuitry 2341 and the scan target area for OCT scanning performed in the subsequent stage. Information obtained by the positional relationship acquiring circuitry 2342 (i.e., the deviation such as a deviation vector or its magnitude) is sent to the deviation comparing circuitry 235.

(S6: Display Checking Screen)

The main controlling circuitry 211 displays a checking screen used for checking the fixation state, on the display device 241. The start timing of displaying the checking screen may be arbitrary. For example, the display of the checking screen can be started at a timing prior to step S1 or at a timing in the period between steps S1 and S5.

Further, the main controlling circuitry 211 displays the observation image whose acquisition has started in step S2, on the checking screen. At this time, the observation image is displayed as a moving image.

Figure 5:
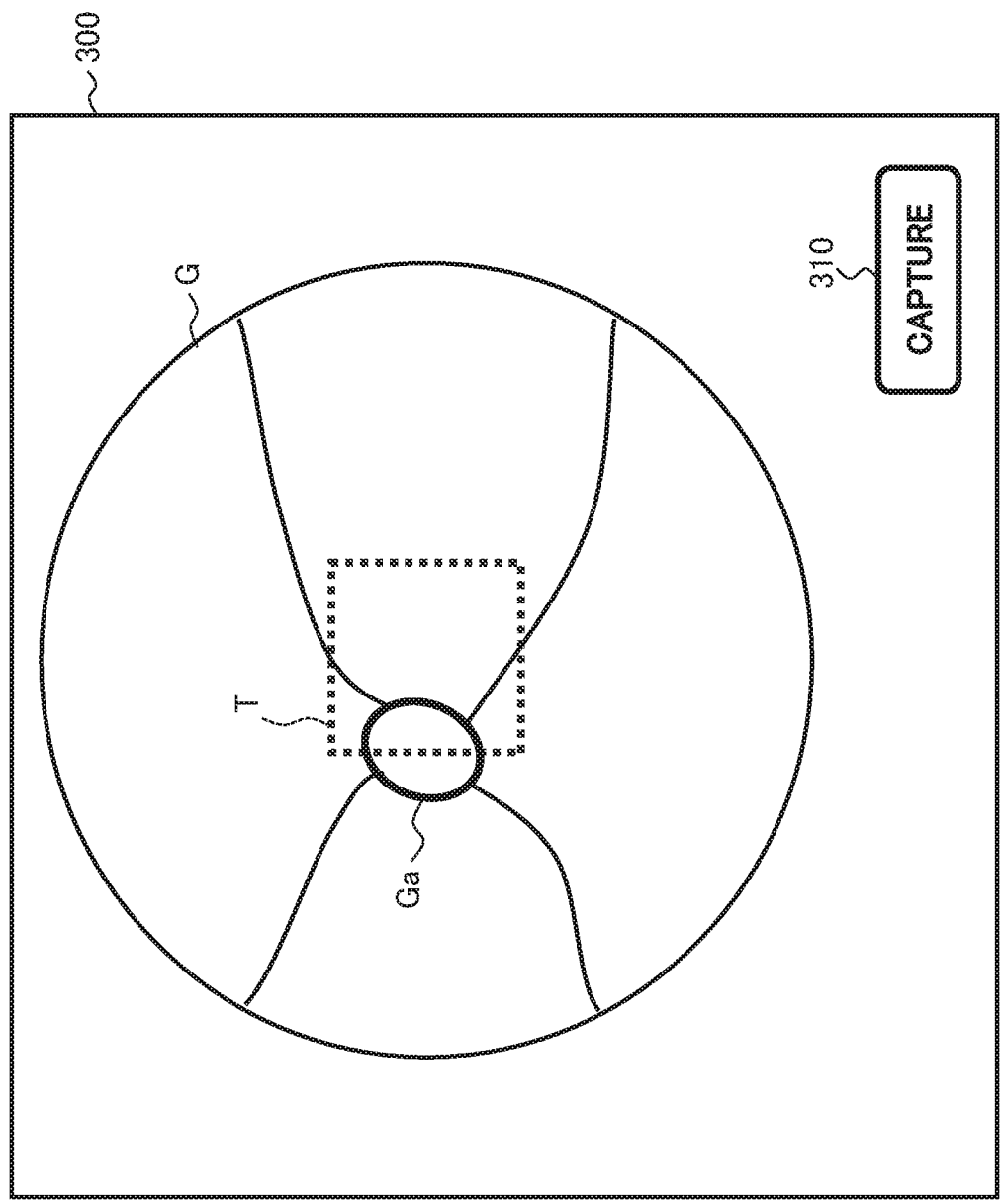
FIG. 5 is a schematic diagram illustrating an example of a screen displayed by the ophthalmological apparatus according to the embodiment.

An example of the checking screen is shown in FIG. 5. On the checking screen 300, the observation image G whose acquisition has been started in step S2 is displayed. The observation image G represents the image of the optic nerve head (optic nerve head image) Ga. Note that there are some cases in which the optic nerve head image Ga is not depicted in the observation image G due to fixation loss, etc.

The checking screen 300 is provided with the capture button 310. The capture button 310 is a software key that receives an instruction for performing OCT imaging. In a typical example, the checking screen 300 displays a pointer (not shown in figures). The user can enter an instruction for OCT imaging by clicking the capture button 310 using the operation device 242. When the display device 241 is a touch panel, the user can enter an instruction for OCT imaging by tapping the capture button 310.

Further, the main controlling circuitry 211 can display an image (a scan target area image) representing the scan target area for OCT scanning, on the checking screen 300. The scan target area image is generated by, for example, the main controlling circuitry 211. The scan target area image is displayed, for example, over the observation image G.

The scan target area image T shown in FIG. 4 represents a target area of alignment for OCT scanning. In the present example, the fixation deviation correction is performed so that the optic nerve head image Ga is located within the scan target area T.

Such a scan target area is determined by the main controlling circuitry 211, for example, according to preset conditions such as the pattern and/or size of the OCT scan, the size of the observation image (e.g., observation magnification), and/or the target site of the OCT scanning (e.g., fixation position).

The form of the scan target area image is not limited to this. For example, a scan target area indicating part or all of the area on which OCT scanning is performed, or a scan target area indicating part or all of the area of an image frame of the observation image can be displayed together with the observation image G.

Although illustration is omitted, the main controlling circuitry 211 can display on the checking screen 300 an image (referred to as an interested site image or an image of the site of interest) based on the position of the predetermined site (e.g., the optical nerve head, the papillary center of gravity) specified by the position specifying circuitry 2341 in step S4. The interested site image is displayed, for example, over the observation image G.

Examples of the interested site image are described. In the first example, the interested site image is an image indicating the position specified by the position specifying circuitry 2341 (e.g., the papillary center of gravity). Such an interested site image may be, for example, a point image displayed at the position in the front projection image H corresponding to the specified position, an arrow image pointing to the specified position, or a like image. In the second example, the interested site image is an image indicating the area of a site targeted in the position specification executed by the position specifying circuitry 2341 (e.g., the outer edge of the optic nerve head).

In addition to or instead of the interested site image, the main controlling circuitry 211 can display, on the checking screen 300, an image (referred to as a positional relationship image) based on the positional relationship acquired by the positional relationship acquiring circuitry 2342 in step S5.

The positional relationship image is displayed over the observation image G, for example.

(S7: Compare Deviation with Threshold)

The deviation comparing circuitry 235 compares the deviation acquired by the positional relationship acquiring circuitry 2342 in step S5 and a predetermined threshold.

(S8: Deviation≤Threshold?)

When the deviation comparing circuitry 235 has determined that the deviation exceeds the threshold (deviation>threshold) by the comparison in step S7 (S8: No), the process proceeds to step S9. On the other hand, when the deviation comparing circuitry 235 has determined that the deviation is equal to or less than the threshold (deviation≤threshold) (S8: Yes), the process proceeds to step S10.

(S9: Control Scan Area/Fixation Position)

When the deviation comparing circuitry 235 has determined that the deviation exceeds the threshold (deviation>threshold) by the comparison in step S7 (S8: No), the main controlling circuitry 211 controls at least one of the scan area for OCT scanning and the display position of the fixation target. The control of the scan area is realized by control of the optical scanner 42. On the other hand, the control of the display position of the fixation target is realized by control of the LCD 39.

The control target (the optical scanner 42 and/or the LCD 39) is determined in advance or determined during the processing. In a typical example, the main controlling circuitry 211 may be configured to control one of the optical scanner 42 and/or the LCD 39 at all times. The determination of the control target may be made, for example, with reference to arbitrary information as the followings: features and/or attributes of the subject; features and/or attributes of the subject's eye; features grasped from the observation image; and features grasped from an examination carried out in the past.

Figure 6A:
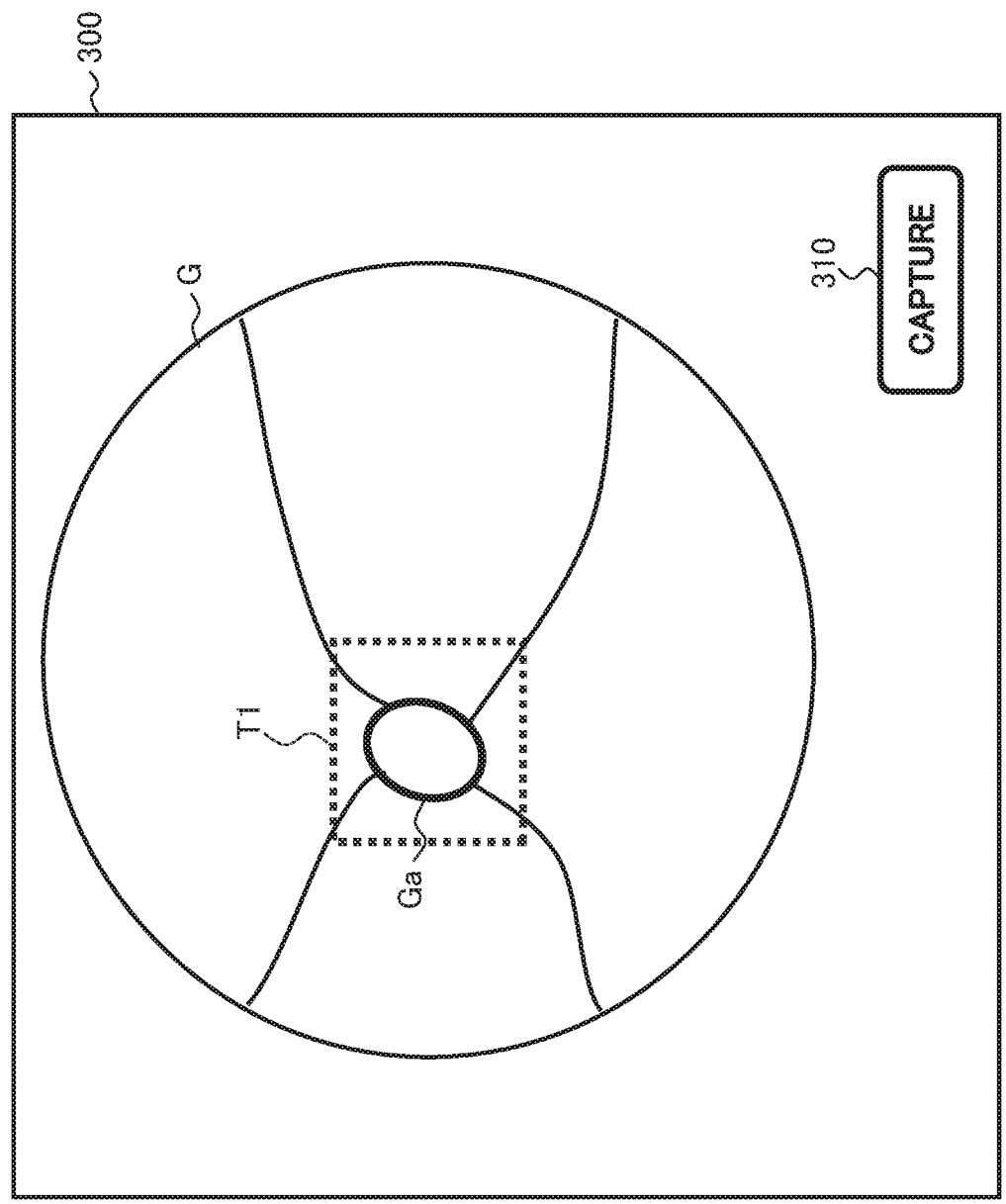
FIG. 6A is a schematic diagram illustrating an example of a screen displayed by the ophthalmological apparatus according to the embodiment.

When controlling the optical scanner 42, for example, the main controlling circuitry 211 shifts the scan area for OCT scanning to cancel out a deviation acquired by the positional relationship acquiring circuitry 2342. In other words, the main controlling circuitry 211 moves the position of the scan target area so that the predetermined site of the fundus Ef (e.g., the optic nerve head) is located inside the scan target area. In this case, for example, as shown in FIG. 6A, the main controlling circuitry 211 can display the new scan target area T1 at a position different from that of the scan target area image T shown in FIG. 5 (i.e., at a position after the shift).

Figure 6B:
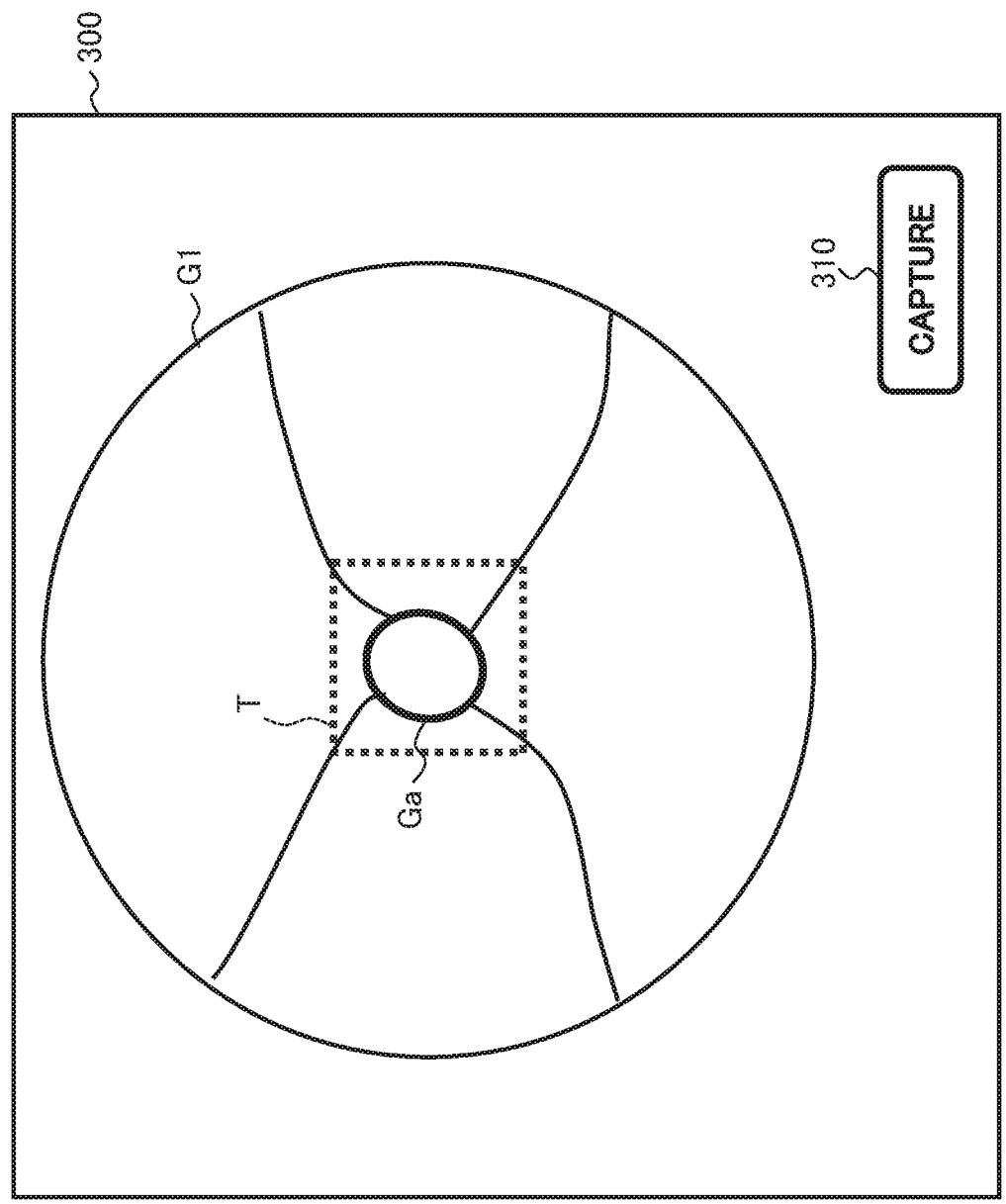
FIG. 6B is a schematic diagram illustrating an example of a screen displayed by the ophthalmological apparatus according to the embodiment.

When controlling the LCD 39, for example, the main controlling circuitry 211 changes the display position of the fixation target to cancel out a deviation acquired by the positional relationship acquiring circuitry 2342. In other words, the main controlling circuitry 211 moves the position of the subject's eye E so that the predetermined site of the fundus Ef (e.g., the optic nerve head) is placed inside the scan target area. In this case, for example, as shown in FIG. 6B, the main controlling circuitry 211 can display the new observation image G1 depicting a region of the fundus Ef different from the observation image G shown in FIG. 5 (i.e., the new observation image G1 depicting a region after the shift).

Such control of the optical scanner 42 and/or the LCD 39 regulates the relative position between the scan area for OCT imaging in the subsequent stage and the subject's eye E (the fundus Ef). More specifically, when controlling the optical scanner 42, the relative position is changed by shifting the scan area. On the other hand, when controlling the LCD 39, the relative position is changed by inducing the movement of the fundus Ef.

After carrying out the control for the optical scanner 42 and/or the LCD 39, the process returns to step S4. Then, steps S4 to S8 are executed again. When the determination is "No" again in step S8, step S9 is executed again and then a routine of steps S4 to S8 is executed again. Such a series of processes is repeated until the determination in step S8 becomes "Yes".

In addition, the ophthalmological apparatus can determine that an error occurs when a predetermined period of time passes from a predetermined timing such as the start of examination or the start of acquisition of the observation image. Alternatively, the user may determine an error. Such error determination is performed when an appropriate fixation state cannot be achieved easily.

(S10: Display "Fixation OK")

On the other hand, when the deviation is determined to be equal to or less than the threshold (deviation≤threshold) by the comparison in step S7 (S8: Yes), the main controlling circuitry 211 displays information indicating that an appropriate fixation state has been achieved, on the checking screen 300.

The information may be predetermined text (character string) or image. For example, texts such as "fixation OK" or "ready for imaging" can be displayed. In addition, it is possible to display a predetermined image that allows the user to intuitively recognize that an appropriate fixation state has been reached.

In another example, the ophthalmological apparatus 1 may be configured to continue displaying information indicating an inappropriate fixation state during the determination is "No" in step S8, and to switch the display content from the information indicating the inappropriate fixation state to information indicating an appropriate fixation state when the determination has become "Yes" in step S8.

(S11: Fundus OCT Imaging)

The user can perceive from the information displayed in step S10 that the appropriate fixation state has been reached. Alternatively, the user can perceive that the appropriate fixation state has been reached by referring to the observation image G.

Once perceiving that the appropriate fixation state has been reached, the user operates the capture button 310 on the checking screen 300. In response to the operation of the capture button 310, the main controlling circuitry 211 controls the optical scanner 42 and the OCT unit 100 to perform OCT imaging of the fundus Ef. Data acquired by the OCT imaging is used for diagnostic imaging and image analysis.

Here, when the scan area has been shifted in step S9, the scan area after the shift is employed for OCT imaging. In addition, when step S9 has been performed twice or more, that is, when the determination has been "No" twice or more in step S8, the scan area set in step S9 executed last is employed for OCT imaging.

When a raster scan etc. is performed in OCT imaging, the three dimensional image constructing circuitry 231 can construct a three dimensional image. Further, the image projecting circuitry 232 can construct a front projection image from the three dimensional image. In addition, the registration processing circuitry 233 can perform registration between the front projection image and the observation image.

(S12: Fundus Photography)

For example, after the completion of the fundus OCT imaging, the main controlling circuitry 211 controls the fundus camera unit 2 to perform photographing of the fundus Ef. Typically, color photography using visible light is performed. The fundus image (captured image, photographed image) obtained in step S12 is used for diagnostic imaging and image analysis together with or separately from the data obtained by the OCT imaging.

When a raster scan etc. is performed in the OCT imaging in step S11, the three dimensional image constructing circuitry 231 can construct a three dimensional image. Further, the image projecting circuitry 232 can construct a front projection image from the three dimensional image. In addition, the registration processing circuitry 233 can perform registration between the front projection image and the photographed image acquired in step S12. This is the end of the processing according to the present operation example.

<Actions and Effects>

Actions and effects of the ophthalmological apparatus according to some embodiment examples will be described.

The ophthalmological apparatus of some embodiment examples includes a light beam projecting system, a fixation system, a photographing device, analyzing circuitry, and controlling circuitry.

The light beam projecting system includes an optical scanner, and is configured to project the light beam onto the fundus of the subject's eye. In the above-described embodiment example, the combination of elements included in the OCT unit 100 and optical elements forming the optical path for guiding the measurement light LS to the subject's eye E, functions as the light beam projecting system.

The ophthalmological apparatus according to some embodiment examples may further include a detector that detects return light of the light beam projected onto the fundus by the light beam projecting system. Such a detector is provided, for example, when the ophthalmological apparatus includes any of the functions of an OCT scanner, a scanning laser ophthalmoscope, an axial length measurement apparatus, a retinal characteristic measurement apparatus, and the like.

The fixation system is configured to project fixation light onto the fundus. In the above-described embodiment example, the combination of the LCD 39 and optical elements forming the optical path for guiding the light (fixation light) output from the LCD 39 to the subject's eye E, functions as the fixation system.

The photographing device is configured to capture a moving image of the fundus onto which the fixation light is being projected by the fixation system, to acquire a front observation image. In the above embodiment example, the combination of the illumination optical system 10 and the photographing optical system 30 functions as the photographing device.

The analyzing circuitry is configured to analyze the front observation image acquired by the photographing device to specify the position of the predetermined site of the fundus. The position specified by the analyzing circuitry is typically a position in the front observation image acquired by the photographing device, that is, a position in the observation target area. In the above embodiment example, the analyzing circuitry 234 functions as the analyzing circuitry.

The controlling circuitry is configured to control at least one of the fixation system and the optical scanner of the light beam projecting system based on the positional relationship between the position of the predetermined site specified by the analyzing circuitry and the projection target area of the light beam from the light beam projecting system. In the above embodiment example, the main controlling circuitry 211 functions as the controlling circuitry.

When controlling the optical scanner, the controlling circuitry can change the projection target area of the light beam based on the positional relationship between the position of the predetermined site specified by the analyzing circuitry and the projection target area of the light beam from the light beam projecting system. In the above embodiment example, the main controlling circuitry 211 changes the projection target area by controlling the optical scanner 42.

When controlling the fixation system, the controlling circuitry can change the fixation position based on the positional relationship between the position of the predetermined site specified by the analyzing circuitry and the projection target area of the light beam from the light beam projecting system. In the above embodiment example, the main controlling circuitry 211 changes the fixation position by controlling the LCD 39.

According to some embodiment examples configured as described above, the relative position between the area onto which the light beam is projected by the light beam projecting system and the subject's eye can be changed, based on the positional relationship between the predetermined site of the fundus (e.g., the papilla center of gravity) and the projection target area. Therefore, when fixation loss occurs (that is, when the positional relationship between the predetermined site of the fundus and the projection target area is not appropriate), the ophthalmological apparatus can regulate the fixation position of the subject's eye and/or the position of the area where the light beam is projected by the light beam projecting system, in order to eliminate the fixation loss. As a result, the ophthalmological apparatus can cope with the fixation loss in an appropriate manner.

In some embodiment examples, the controlling circuitry may be configured to display the front observation image acquired by the photographing device on a display device. Further, the controlling circuitry may be configured to display an image indicating the projection target area of the light beam from the light beam projecting system, over the front observation image. In the above embodiment example, the display device 241 functions as the display device. In addition, in the above embodiment example, the scan target area image T is displayed as the image indicating the projection target area.

According to the embodiment configured as described above, the user can observe the predetermined site of the fundus, grasp the projection target area of the light beam, and grasp the relative position between the predetermined site of the fundus and the projection target area.

In such embodiments, the controlling circuitry may be configured to further display an image representing the position of the predetermined site of the fundus over the front observation image. In the above embodiment example, the interested site image corresponds to the image representing the position of the predetermined site of the fundus.

In some embodiment examples, the controlling circuitry may be configured to compare the deviation between the projection target area of the light beam and the position of the predetermined site of the fundus specified by the position specifying circuitry, with a predetermined threshold, and further execute control for at least one of the fixation system and the optical scanner of the light beam projecting system only when the deviation exceeds the predetermined threshold.

According to such embodiment examples, when the deviation of the projection target area with respect to the position of the predetermined site of the fundus is large, the ophthalmological apparatus can execute control for eliminating the fixation loss. In addition, when the deviation becomes sufficiently small, the ophthalmological apparatus can proceed to an examination (e.g., measurement, imaging).

The embodiments described above are only examples of the present invention. Those who intend to implement the present invention can make any modifications (e.g., omissions, substitutions, replacements, additions) within the scope of the gist of the present invention.

EXPLANATION OF SYMBOLS

1 ophthalmological apparatus
10 illumination optical system
30 photographing optical system
39 LCD
42 optical scanner
100 OCT unit
211 main controlling circuitry
234 analyzing circuitry
2341 position specifying circuitry
2342 positional relationship acquiring circuitry
235 deviation comparing circuitry
241 display device

The invention claimed is:

1. An ophthalmological apparatus comprising:
a light beam projecting system that includes an optical scanner and projects a light beam onto a fundus of a subject's eye;
a fixation system that projects fixation light onto the fundus;
a photographing device that captures a moving image of the fundus onto which the fixation light is being projected to acquire a front observation image;
analyzing circuitry that analyzes the front observation image to specify a position of a predetermined site of the fundus; and
controlling circuitry that controls at least one of the fixation system and the optical scanner based on a positional relationship between the position of the predetermined site specified by the analyzing circuitry and a projection target area of the light beam from the light beam projecting system, wherein
the controlling circuitry compares a deviation of the position of the predetermined site with respect to the projection target area of the light beam with a predetermined threshold, and executes control for at least one of the fixation system and the optical scanner only when the deviation exceeds the predetermined threshold.

2. The ophthalmological apparatus of claim 1, wherein the controlling circuitry controls the optical scanner to change the projection target area of the light beam based on the positional relationship.

3. The ophthalmological apparatus of claim 1, wherein the controlling circuitry controls the fixation system to change a fixation position based on the positional relationship.

4. The ophthalmological apparatus of claim 1, wherein the controlling circuitry displays the front observation image on a display device, and displays an image indicating the projection target area of the light beam over the front observation image.

5. The ophthalmological apparatus of claim 4, wherein the controlling circuitry displays an image representing the position of the predetermined site over the front observation image.

* * * * *